US006379914B1

(12) United States Patent
Pasco

(10) Patent No.: US 6,379,914 B1
(45) Date of Patent: Apr. 30, 2002

(54) METHOD AND APPARATUS FOR MEASURING USE OF A SUBSTRATE IN A MICROBIALLY CATALYZED REACTION

(75) Inventor: Neil Pasco, Christchurch (NZ)

(73) Assignee: Lincoln Ventors Limited, Canterbury (NZ)

( * ) Notice: Subject to any disclaimer, the term of this patent is extended or adjusted under 35 U.S.C. 154(b) by 0 days.

(21) Appl. No.: 09/308,628

(22) PCT Filed: Nov. 26, 1997

(86) PCT No.: PCT/NZ97/00158

§ 371 Date: May 26, 1999

§ 102(e) Date: May 26, 1999

(87) PCT Pub. No.: WO98/23770

PCT Pub. Date: Jun. 4, 1998

(30) Foreign Application Priority Data

Nov. 26, 1996 (NZ) ................................ 299827

(51) Int. Cl.[7] .............. C12Q 1/26; C12Q 1/02; G01N 27/00; G01N 21/00
(52) U.S. Cl. ............... 435/25; 435/29; 422/79; 422/82.02; 422/82.05
(58) Field of Search ................. 435/25, 29, 287.5, 435/801; 210/606, 758, 605, 750, 753; 422/78, 79, 82.01, 82.05, 82.02; 71/10

(56) References Cited

U.S. PATENT DOCUMENTS

| | | | |
|---|---|---|---|
| 3,725,236 A | 4/1973 | Johnson, Jr. ............... 204/195 |
| 3,857,761 A | 12/1974 | Cummings .................... 204/1 |
| 4,476,224 A | 10/1984 | Adler ......................... 435/253 |
| 5,085,759 A | 2/1992 | Harker ........................ 204/408 |
| 5,413,690 A | 5/1995 | Kost et al. .................. 204/403 |
| 5,518,893 A | 5/1996 | Park et al. ................... 435/29 |
| 5,589,133 A | 12/1996 | Suzuki ......................... 422/79 |

FOREIGN PATENT DOCUMENTS

| | | | | |
|---|---|---|---|---|
| EP | 136362 A | 4/1985 | .......... | G01N/27/30 |
| EP | 0193420 A1 | 9/1986 | ............ | C12Q/1/00 |
| EP | 0255291 | 2/1988 | | |
| EP | 0470649 A2 | 2/1992 | ............ | C12Q/1/26 |
| GB | 2189605 | 10/1987 | | |
| JP | 62160193 A | 7/1987 | ............. | C02F/3/00 |
| JP | 08015211 A | 1/1996 | ......... | G01N/27/327 |

OTHER PUBLICATIONS

FREBE et al. Derwent Acc. No. 1992–080804. DD 294798 A, abstract only. (Oct. 1991).

Derwent Abstract Accession No. 97–035237/04, Class X25, DE 19521181 A (Reimann), Dec. 12, 1996.

Derwent Abstract Accession No. 88–148033/22, Class S03, DD 253045 A (AKAD Wissenschaft DDR), Jan. 6, 1988.

*Primary Examiner*—Michael P. Woodward
*Assistant Examiner*—Marjorie A Moran
(74) *Attorney, Agent, or Firm*—Jacobson Holman, PLLC

(57) ABSTRACT

A sample substrate in a microbially catalysed biochemical reaction is measured by incubating the substrate with an excess of a microorganism and an excess of a co-substrate until the substrate is oxidized to a predetermined end point, and measuring the quantity of reduction of the co-substrate.

15 Claims, 1 Drawing Sheet

METHOD AND APPARATUS FOR MEASURING USE OF A SUBSTRATE IN A MICROBIALLY CATALYZED REACTION

This is the national stage filing under 35 USC 371 of PCT/NZ/00158, filed Nov. 26, 1997.

TECHNICAL FIELD

This invention relates to a method of measuring a reactant consumed in a biological reaction. More particular, it relates to a quantitative method for the measurement of the consumption of a substrate in a microbially catalysed reaction. Preferably, it relates to the measurement of biochemical oxygen demand (BOD) of a sample by determining the equivalent mediator demand or alternatively the measurement of the biological toxicity of a sample by the perturbation in quantity of mediator conversion induced by the presence of the sample.

BACKGROUND ART

Biochemical oxygen demand is the amount of oxygen taken up owing to the respiratory activity of microorganisms growing on organic compounds present in a water sample when incubated at 20° C. for a fixed period (usually five days). It is a measure of the degree of organic pollution of water.

A disadvantage in the conventional method of measuring BOD is that it can take up to five days to do so partly because of the low level of solubility of oxygen in water and partly because of the low microbial concentration in the seed material.

Non-biological methods for rapidly determining the BOD of a sample are described in U.S. Pat. Nos. 3,725,236 and 3,857,761. These patents relate to substantially exhaustive electrochemical oxidation of an aqueous sample in an apparatus for forming oxygen which is measured to calculate BOD.

U.S. Pat. No. 5,085,757 describes another apparatus for rapidly determining BOD of a liquid at an on-site location. The apparatus is a very elaborate one. The method of determining BOD involves a biochemical reaction using a culture medium and measuring the change in the dissolved oxygen content over a period of time and calibrating to determine BOD.

U.S. Pat. No. 5,518,893 is directed to a rapid method of determining BOD. A known microorganism culture is aerated to exhaust the organic matter available to the microorganisms. A sample of liquid to be tested is added and the amount of oxygen consumed by the microorganisms is determined and from this the BOD is calculated. An apparatus for conducting the measurement is described.

GB 2,189,605 describe method for detecting pollution in a continuous liquid flow. The method involves taking a portion of the flowing liquid and adding it to a compatible electron transfer mediator. The mixture is fed into a sensor cell containing bacteria. An activity of the bacteria is stimulated and the level of activity at an electrode in the cell is measured by electron transfer from the mediator.

EP 255291 and EP 470649 both describe methods and an apparatus for making electrochemical measurements or detection of a component of an aqueous liquid sample. The sample containing the component to be analysed is allowed to produce a corresponding quantity of an electrochemically oxidisable or reducible substance. This is then electrochemically oxidised or reduced and the quantity of oxidisable or reduceable substance in the cell is measured as an index of the quantity of the substance.

U.S. Pat. No. 5,413,690 relates to a potentiometric biosensor test strip and a method for detection or measurement of an analyte from a fluid sample. This is done by measuring the change in potential of the system as a result of the chemical reaction of analyte, enzyme and mediator.

It is an object of one aspect of this invention to provide alternatives to the described apparatus and processes or at least to offer the public a useful choice.

DISCLOSURE OF THE INVENTION

Accordingly, the invention may be said broadly to consist of a method of measuring the consumption of a sample substrate in a microbially catalysed biochemical reaction which comprises incubating said substrate with an excess of a microorganism and an excess of a co-substrate until said substrate is oxidised to a predetermined end point and measuring the quantity of reduction of said co-substrate.

In one embodiment the method is used to determine the BOD of said sample substrate.

In another embodiment the method is used to determine the biological toxicity of said sample substrate.

Preferably said reaction is conducted under anaerobic conditions.

In one embodiment said predetermined end point is reached when the rate of change in the reduced co-substrate to oxidised substrate ratio is no longer significant.

In another embodiment said sample substrate and said co-substrate are separated from said microorganism before measuring the quantity of reduction of said co-substrate.

In one embodiment said quantity of reduction of said co-substrate is measured by an electrochemical method.

Alternatively, said quantity of reduction of said co-substrate is measured by an optical method.

Preferably, said electrochemical method is either bulk electrolysis or potentiometry.

Preferably, said optical method is either colorimetry or fluorometry.

In another alternative said quantity of reduction of said co-substrate is measured by reoxidising said mediator and measuring the charge for doing so.

Preferably, said sample substrate contains an organic pollutant.

Alternatively, said sample substrate contains a nutrient pollutant.

Preferably, said micro-organism is any one of *Escherichia coli, Proteus vulgaris, Torulopsis candida, Bacillus subtilis, Trichosporon cutaneum* and *Saccharomyces cerevisiae.*

In one alternative, said microorganism is *E. coli.*

In another alternative said microorganism is *P. vulgaris.*

Preferably, said co-substrate is any one of benzoquinone, dichlorophenolindophenol, methylene green, methylene blue, phenazine methosulphate, potassium hexacyanoferrate (III), resorufin, thionine, toluidene-blue-O.

Preferably, said anaerobic conditions are maintained by sparging the incubation container in which said incubation is carried out with oxygen free nitrogen.

Preferably, said reoxidation of co-substrate and measurement of charge are carried out in a bulk electrolysis cell.

Preferably, the measured charge is converted to a standard BOD measurement.

Preferably, when necessary said incubation is terminated by filtering said co-substrate, sample substrate and microorganism through a filter whose pore size is such that the co-substrate substrate is in the filtrate and substantially all of the microorganism is in the retentate.

Preferably, the pore size of said filter is 0.45 μm.

Preferably, said co-substrate is a mediator.

The invention may also be said broadly to consist in a method of measuring biochemical oxygen demand substantially as herein described with reference to the examples and FIG. 1.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

MODES OF CARRYING OUT THE INVENTION

Standard BOD Measurement (Dilution Method)

Figure 1:
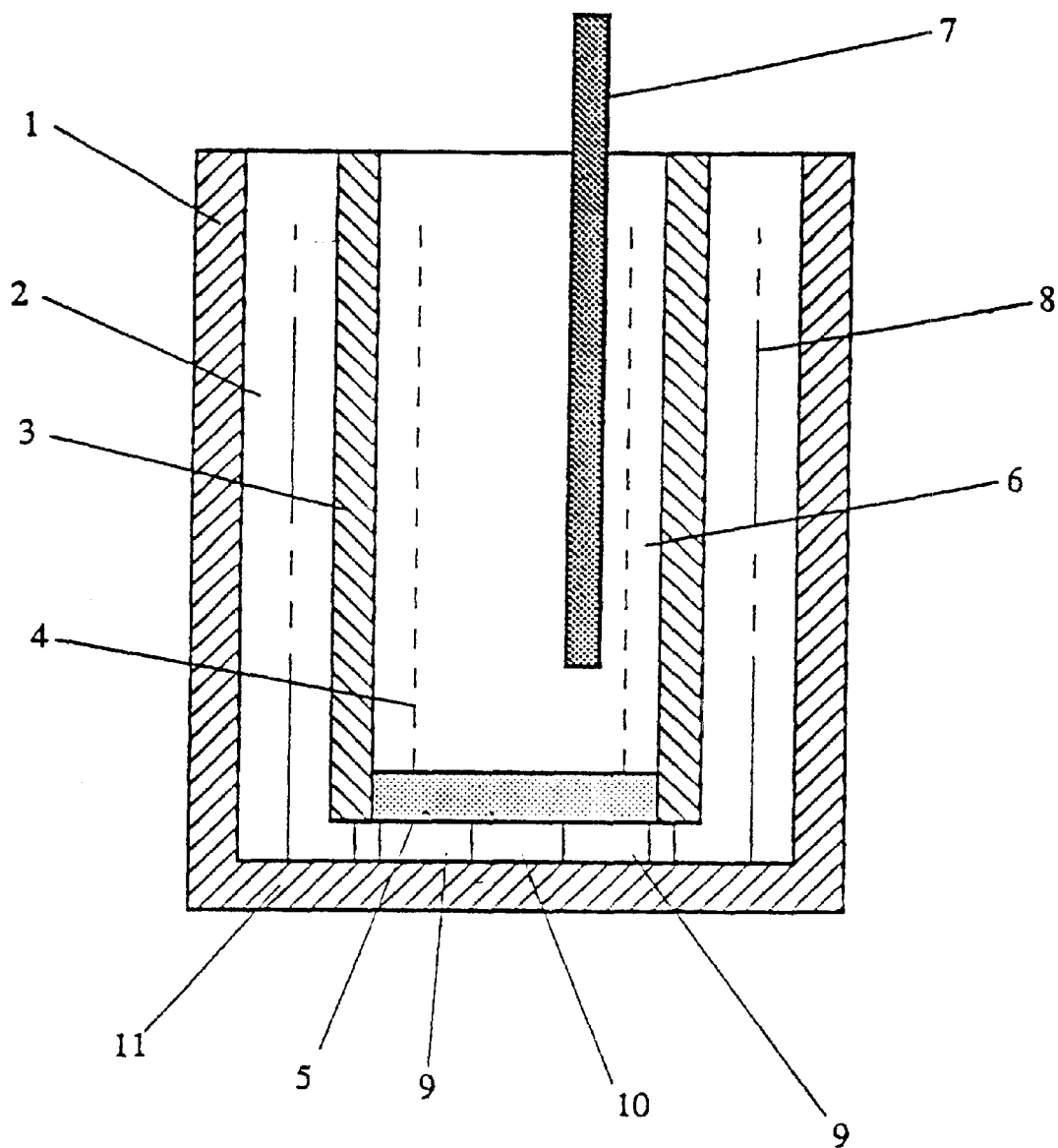
FIG. 1 is a cross-sectional view of a bulk electrolysis cell in which the charge for reoxidising a mediator in a method according to the invention may be measured.

BOD is a measurement of the amount of oxygen, expressed in mg/l or parts per million (ppm), required in the biological oxidation of nutrients or other pollutants by micro-organisms. Traditionally the amount of oxygen consumed in the biological oxidation process is calculated by comparing the amount of residual oxygen left after five days of microbial oxidation with the amount measured in the sample at the beginning. During the five day period of a BOD test, the micro-organisms oxidise mainly the soluble organic matter present in the sample. The traditional BOD method consists of placing a sample in a full airtight bottle under specified conditions for a specified time. Dissolved oxygen is measured initially and after incubation. The BOD is computed from the difference between the initial and final dissolved oxygen. The test measures the oxygen required for the biological oxidation of organic material (carbonaceous demand) and the oxygen used to oxidise inorganic material such as sulphides and ferrous iron. In the following equations the pollutant whose BOD is being measured is referred to as the substrate. A generalised reaction equation for the oxidation of organic material can be written as:

$$C_xH_yO_z + nO_2 \rightarrow xCO_2 + y/2 H_2O \quad (1)$$

or $$\text{substrate}_{red} + nO_2 \rightarrow \text{substrate}_{ox} + H_2O \quad (2)$$

The amount n thus represents the oxygen demand and this quantity is calculated from the measurement of initial and final dissolved oxygen. The mechanism which micro-organisms use to perform the biological oxidation is known as the respiratory chain or the electron transport chain. The function of this sequence is to accept electrons from reduced compounds and transfer them ultimately to oxygen. Oxygen therefore behaves as the terminal electron acceptor in the electron transport chain of micro-organisms.

Mediators

Mediators are typically low molecular weight substances that function as alternative electron acceptors to the co-substrate oxygen. Some mediators have the ability to interact within the micro-organism's electron transport chain and the progress of a biological oxidation should be able to be followed by monitoring the status of the mediator rather than oxygen. Previous work (Baronian and Pasco, 1993) and others (Ramsey and Turner, 1988) has demonstrated the ability of the mediator hexacyanoferrate(III) to act as an electron acceptor in the microbial oxidation of glucose by the bacterium E.Coli. It is believed that the mediator is reduced by one of the redox proteins in the respiratory cycle of E.Coli, with hexacyanoferrate(III) replacing oxygen in the respiratory cycle. Mediators have the ability to reversibly react at the electrode and at a lower anodic potential than oxygen, reducing the possibility of interference by other easily oxidised species. The reaction is completely independent of oxygen, permitting the sensor to function in anaerobic environments.

Mediators are the preferred co-substrates according to this invention.

Bulk Electrolysis with Coulometry

In this technique an analyte is either completely or partially electrolysed by applying either a fixed potential or a fixed current to an electrode. The current is integrated during the course of the electrolysis and the total charge is used to calculate the amount of material electrolysed. Reduced mediator, generated in the microbial oxidation stage, is the analyte and is quantitatively converted back to its oxidised form at the anode of a bulk electrolysis cell. The total charge is a measure of the amount of mediator electrolysed at the anode. The method is absolute, no standard reagents are required. The electrolysis can be performed very rapidly by using electrodes with high surface area, separate anolyte and catholyte compartments, and maintenance of stirring.

Biochemical Oxygen Demand by Bulk Electrolysis of Mediator

Rather than monitor the uptake of oxygen, in the method of this invention the biological reduction of a mediator is monitored and the consumption of mediator is measured by the quantity of charge required for its reoxidation in a bulk electrolysis cell. The generalised equation (Equation 2) when a mediator functions as the alternative electron acceptor in a microbially catalysed biological oxidation can be rewritten as:

$$\text{substrate}_{red} + \text{mediator}_{ox} \xrightarrow[\text{catalysis}]{\text{microbial}} \text{substrate}_{ox} + \text{mediator}_{red} \quad (3)$$

The quantity of reduced mediator produced by the biological oxidation of mediator (Equation 3) can be determined at any stage by bulk electrolysing the mediator back to its oxidised form.

$$\text{mediator}_{red} \rightarrow \text{mediator}_{ox} + e^- \quad (4)$$

The quantity of charge for the reoxidation of the mediator (Equation 4) is a direct measure of the amount of oxidation deriving from the microbially catalysed process (Equation 3) and this quantity is obtained from integration of the current (coulometry) during the course of the electrolysis. The mediated biological reaction (Equation 3) is a solution phase reaction and can occur quite independently of the electrolysis reaction. The extent of the microbial oxidation can be measured at any time by electrolysing the reduced mediator.

Both the microbial conversion and the electrolytic reconversion can take place in the same vessel if desired.

The bulk electrolysis method avoids the necessity of immobilising either the micro-organisms or the mediator and the amount of biologically reduced mediator can be quantitatively determined by measuring the charge to electrolyse it back to the oxidised state. This technique therefore provides an alternative measurement of the oxygen demand by measuring the equivalent mediator demand.

Mediator Requirements

Preferred mediators for use in the method of the invention have:
- an ability to interact within the micro-organism's electron transport chain;
- stability in biological environment (aqueous solution, pH and ionic strength appropriate to organism);
- stability in both the oxidised and reduced forms;
- non-toxicity to micro-organisms; and
- preferably low redox potential.

A number of mediators fulfil all these requirements, some partially. The following non-exhaustive list includes mediators that have been used in conjunction with micro-organisms: benzoquinone, dichlorophenolindophenol, methylene green, methylene blue, phenazine methosulphate, potassium hexacyanoferrate (III), resorufin, thionine, toluidene-blue-O. Other suitable mediators will be known to those skilled in the art.

In the method according to the invention the measurement is carried out by measuring the quantity of mediator converted in a microbially catalysed redox reaction where the quantities of microbial cells and mediator are in excess relative to the sample. The time taken for sample conversion is minimised by the initial conditions and the sample becomes the rate limiting reagent. The amount of mediator converted is readily determined (for example using electrochemical or optical techniques) and is a measure of the substrate converted which in turn is related to the microbial activity. The short duration required for a substantial conversion of substrate brought about by the use of a high initial concentrations of microbial cells and mediator provides a very rapid method for the determination of the quantity of sample present.

The advantages of this method will be demonstrated by the following non-limiting examples.

EXAMPLE 1
Growth of Bacteria

*E. coli* cells were cultured overnight in a trypticase soy growth broth, harvested and resuspended in a phosphate buffered saline solution (0.05M $KH_2PO_4/K_2HPO_4$ pH7 and 0.1M KCl) to an optical density ($OD_{600}$) of 0.380.

EXAMPLE 2
Cellular Reduction of Mediator without Substrate

Fresh microbial cells have the facility to reduce redox mediators in the absence of exogenous substrates, such as glucose or glutamic acid but this endogenous response decays as the cells age if they are maintained in a minimal medium. A mixture, made up from 18 ml of an *E.coli* suspension and 5.4 ml of potassium hexacyanoferrate (III), was incubated for 30 minutes. Microbial action was terminated by filtering the mixture are through a 0.45 μm filter to separate the *E.coli* from the mixture.

EXAMPLE 3
Cellular Reduction of Mediator with Substrate

A mixture, made up from 18 ml of resuspended *E.coli*, 5.4 ml of 0.25M potassium hexacyanoferrate (III) and 0.9 ml of 0.025M glucose, was incubated for 30 minutes. Microbial action was terminated by filtering the mixture through a 0.45 μm filter.

EXAMPLE 4
Bulk Electrolysis

Reduced mediator, generated by cellular reduction as described in examples 2 and 3, was quantitatively reoxodised using a bulk electrolysis with coulometry method. This is described with reference to the electrolysis cell in FIG. 1.

The bulk electrolysis apparatus used in the method of this invention comprises an outer vessel, 1 (glass), to contain the reaction ingredients. The vessel is separated into anolyte compartment 6, and catholyte compartment 2 by an inner vessel 3. Interchange of soluble species and ions can take place via a sintered glass disk 5 forming the bottom of inner vessel 3. Cylindrical platinum gauze electrodes are used for both the anode 4 and the cathode 8. An Ag/AgCl reference electrode 7 is provided within anolyte compartment 6 in inner vessel 3. The inner vessel 3 has a series of semi-circular feet 9 which space it vertically from the bottom 11 of vessel 1. There are gaps 10 between these feet so that catholyte can flow freely through the area between the bottom of disk 5 and the top of bottom 11.

The potential of the anode 8 was set at +400 mV relative to the Ag/AgCl reference electrode 7 during bulk electrolysis. Rest potentials were measured prior to and at the completion of each bulk electrolysis. The anolyte comprises the reduced mediator from the incubation reaction (examples 2 and 3). The composition of the catholyte is not critical. Aqueous solutions of buffer or oxidised mediator as described for the anolyte were used.

EXAMPLE 5
BOD Determination of Substrate (Control)

The BOD of the substrate solution was determined independently using a Hach Manometric BOD apparatus. The standard procedure, outlined in the Hach Manometric BOD apparatus Model 2173A manual and Hach BOD Technical Information Series (Booklet 7), were followed. *E.coli* suspension ($OD_{600}$ 0.380) was used as seed bacteria. Glucose (0.9 ml, 0.025M) in a total volume of 24.4 ml is equivalent to a concentration of 165 mg/l and a BOD demand of 121 mg/l. Standard solutions of BOD 200 (glucose 150 mg/l, glutamic acid 150 mg/l) and BOD 100 (glucose 150 mg/l) were prepared and duplicate BOD measurements taken along with the BOD of the seed *E.coli* suspension.

EXAMPLE 6
Cellular Reduction of Mediator without Substrate

The amount of charge, required for reoxidising microbially reduced mediator after a 30 minute incubation, was measured using the bulk electrolysis method described in example 4. Electrolysis was terminated when the current diminished to 1% of its initial value. Four samples were determined and the results are shown in Table 1.

TABLE 1

| | Reduction of Mediator, No Substrate | | |
|---|---|---|---|
| Run # | $OD_{600}$ | Fe(III)/μmol | $Q_{1\%}$/coulomb |
| 37 | .388 | 1350 | 0.299 |
| 39 | .388 | 1350 | 0.266 |
| 41 | .388 | 1350 | 0.254 |
| 43 | .388 | 1350 | 0.285 |

EXAMPLE 7
Cellular Reduction of Mediator with Substrate

The amount of charge, required for reoxidising microbially reduced mediator in the presence of exogenous substrate (D-glucose, 0.025M) after a 30 minute incubation, was measured using the bulk electrolysis method described in example 4. The results are shown in Table 2.

TABLE 2

Reduction of Mediator With Added Substrate

| Run # | $OD_{600}$ | Fe(III)/$\mu$mol | Glucose/$\mu$mol | $Q_{1\%}$/coulomb |
|---|---|---|---|---|
| 42 | 0.388 | 1350 | 22.5 | 0.735 |
| 44 | 0.388 | 1350 | 22.5 | 0.770 |
| 46 | 0.388 | 1350 | 22.5 | 0.722 |
| 47 | 0.407 | 1350 | 22.5 | 0.696 |
| 54 | 0.401 | 1350 | 22.5 | 0.732 |

The results obtained in Tables 1 and 2 show that the microbially catalysed reduction of mediator is increased in the presence of substrate. The mean of the four endogenous responses in Table 1 is 0.276 coulomb while the mean of the measurements of Table 2 with added substrate is 0.731 coulomb. The difference is significant but much less than what would be expected on the basis of complete conversion of the substrate. Stoichiometric oxidation of 1 $\mu$mol of glucose produces 24 $\mu$mol of reduced mediator (potassium hexacyanoferrate (II) ) and is equivalent to 2.316 coulomb. The theoretical charge required for the complete oxidation of 22.5 $\mu$mol of glucose is 52.1 coulomb. The bulk electrolysis measurements in Table 2 demonstrate that only a small fraction, about 1% on the basis of these figures, of the available glucose is being microbially oxidised in the 30 minute incubation period. This is indicative of excess substrate. To achieve greater conversion either the microbial cell concentration can be increased or the substrate concentration decreased.

EXAMPLE 8
Reduction of Mediator with Substrate Dilution

The effect of decreasing the exogenous substrate (D-glucose) concentration was examined by serial, 10-fold dilution of the 0.025M glucose. These results are shown in Table 3.

TABLE 3

Effect of Substrate Dilution

| Run # | $OD_{600}$ | Fe(III)/$\mu$mol | Glucose/$\mu$mol | $Q_{1\%}$/coulomb |
|---|---|---|---|---|
| 46 | 0.407 | 1350 | 22.500 | 0.722 |
| 47 | 0.407 | 1350 | 22.500 | 0.696 |
| 48 | 0.407 | 1350 | 2.2500 | 0.685 |
| 49 | 0.407 | 1350 | 2.2500 | 0.685 |
| 50 | 0.407 | 1350 | 0.2250 | 0.370 |
| 51 | 0.407 | 1350 | 0.2250 | 0.348 |
| 52 | 0.407 | 1350 | 0.0225 | 0.249 |
| 53 | 0.407 | 1350 | 0.0225 | 0.226 |

In Table 3 there is an insignificant change in the coulombs recorded until the concentration of substrate is diluted 100-fold or greater. Although the signal is now significantly different to its previous level, it is no longer significantly different from the signal recorded by the endogenous response alone. At this concentration of microbial cells and with an incubation period of only 30 minutes the method is incapable of discriminating between substrate and no substrate.

EXAMPLE 9
Reduction of Mediator with Varying Incubation Times

BOD 200 mg/l standard solutions (glucose 150 mg/l, glutamic acid 150 mg/l ) were used as substrate and the effects of varying microbial incubation times were evaluated. The suspension of cells and mediator matched that used in examples 1 to 8. The effect of variation of incubation time is shown in Table 4.

TABLE 4

Effect of Incubation Time

| Run # | $OD_{600}$ | Glu/$\mu$mol | Gla/$\mu$mol | Time/min | $Q_{1\%}$/coulomb |
|---|---|---|---|---|---|
| 54 | 0.401 | 22.500 | 0 | 30 | 0.732 |
| 55 | 0.401 | 0.507 | 0.621 | 30 | 0..488 |
| 56 | 0.401 | 0.507 | 0.621 | 60 | 0.595 |
| 57 | 0.401 | 0.507 | 0.621 | 120 | 1.242 |
| 58 | 0.401 | 0.507 | 0.621 | 240 | 1.430 |
| 59 | 0.401 | 0.507 | 0.621 | 1260 | 1.895 |

The cells used in this example were the same batch of cells used in example 8, except that they were one day older. Run 54 replicates the conditions of example 7 and the good agreement between the measurements in tables 2, 3 and 4 demonstrates that the method is not sensitive to cell age in the short term. The total charge for the complete conversion of the amount of glucose and glutamic acid available in Runs 55 through 59 is calculated to be 2.67 coulomb. The oxidation of glucose by microbial cells has been reported as having a coulombic efficiency of about 50% (Thurston et al., 1985). The results in Table 4, using cells at $OD_{600}$ 0.401, demonstrate that an incubation period between 2 and 4 hours is required to generate an amount of reduced mediator equivalent to a 50% conversion. The results set out in Tables 3 and 4 suggest that to attain a 100% microbial conversion of the substrate in less than 60 minutes a 1000-fold increase in the concentration of microbial cells was necessary.

EXAMPLE 10
Reduction of Mediator with Elevated Microbial Cell Concentration

*E. coli* cells were cultured overnight in a Trypticase soy growth broth, harvested and resuspended in a phosphate buffered saline solution (0.05M $KH_2PO_4/K_2HPO_4$ pH7 and 0.1M KCl) to an $OD_{600}$ of around 5.5.

TABLE 5

Effect of Incubation Time at High Cell Concentration. Substrate Response

| Run # | $OD_{600}$ | Fe(III)/$\mu$mol | Glucose/$\mu$mol | Time | $Q_{1\%}$/coulomb |
|---|---|---|---|---|---|
| 60 | 5.720 | 830 | 1.522 | 30 | 2.913 |
| 61 | 5.720 | 830 | 1.522 | 60 | 5.774 |
| 62 | 5.720 | 830 | 1.522 | 120 | 7.926 |
| 63 | 5.720 | 830 | 1.522 | 240 | 9.761 |

The theoretical charge required for the complete oxidation of 1.522 $\mu$mol of glucose is 3.525 coulomb. The 30 minute result could be interpreted as a conversion exceeding 80%. However, at times of 60 minutes and beyond, we observed charges well in excess of the theoretical amount, indicative that the endogenous response of the micro-organisms or some other mechanism was contributing a substantial portion of the accumulated charge.

EXAMPLE 11
Reduction of Mediator with Varying Incubation Times at High Cell Concentration A parallel series of measurements were performed to measure the endogenous contribution. In these measurements, mediator alone was incubated with cells of the same batch as used in example 10. The results are set out in Table 6.

TABLE 6

Effect of Incubation Time at High Cell Concentration. Endogenous Response.

| Run # | $OD_{600}$ | Fe(III)/$\mu$mol | Glucose/$\mu$mol | Time | $Q_{1\%}$/coulomb |
|---|---|---|---|---|---|
| 64 | 5.670 | 830 | 0 | 30 | 2.708 |
| 65 | 5.670 | 830 | 0 | 60 | 5.291 |
| 66 | 5.670 | 830 | 0 | 120 | 8.970 |
| 67 | 5.670 | 830 | 0 | 240 | 10.090 |

These results demonstrate that any signal arising as a result of the microbially catalysed interaction with substrate is being overwhelmed by the level of endogenous conversion.

EXAMPLE 12
Reduction of Mediator with High Cell Concentration and Anaerobic Conditions The above measurements were repeated except that anaerobic conditions were maintained by sparging the reactants with oxygen-free nitrogen, prior to and throughout the incubation phase. A sample of fresh microbial cells, $OD_{600}$ 5.440, was split into two equal portions. To one portion, a mixture of mediator and substrate was added, the second portion was mixed with mediator alone. Each portion was incubated over 120 minutes, with a sample taken for bulk electrolysis determination every 60 minutes. The results are set out in Table 7.

TABLE 7

High Cell Concentration and Anaerobic Conditions

| Run # | $OD_{600}$ | Fe(III)/$\mu$mol | Glucose/$\mu$mol | Time | $Q_{1\%}$/coulomb |
|---|---|---|---|---|---|
| 70 | 5.440 | 1105 | 0 | 60 | 2.362 |
| 71 | 5.440 | 1105 | 0 | 120 | 3.057 |
| 68 | 5.440 | 794 | 3.122 | 60 | 8.142 |
| 69 | 5.440 | 794 | 3.122 | 120 | 9.166 |

The theoretical charge required for the complete oxidation of 3.122 $\mu$mol of glucose is 7.207 coulomb. At 60 minute the difference between the substrate dependent response and the endogenous response is 5.8 coulomb, at 120 minutes this difference is 6.1 coulomb. The combination of high cell concentration and anaerobic environment throughout the incubation phase provides conditions for a higher percentage substrate conversion. The difference between the electrochemical signal recorded with and without substrate is now very substantial and these figures are indicative of an 80% conversion of the available substrate at 60 minutes and 85% conversion at 120 minutes.

Further refinement and optimisation of the incubation phase provide conditions for almost complete substrate conversion in less than 60 minutes and in combination with bulk electrolysis or potentiometric measurements provide a basis for the rapid determination of BOD.

Other permutations and combinations within the scope of the invention will be apparent to those skilled in the art.

Using a standard BOD solution it is possible to convert the charge for reoxidising the mediator into a standard BOD equivalent.

The generalised reaction, equation (1), for the complete oxidation of organic material can be rewritten when the substrate is glucose as:

$$C_6H_{12}O_6 + 6O_2 \rightarrow 6CO_2 + 6H_2O \qquad (5)$$

The stoichiometric oxidation of each mole of glucose requires 6 moles of oxygen as co-substrate. A 300 mg/l solution of glucose is reported to have a $BOD_5$ of 200 mg/l (APHA 1995). On a molar basis 300 mg/l of glucose corresponds to 1.67 mM and the stoichiometric oxygen requirement is 10 mM. The BOD requirement of 200 mg/l converts to 6.25 mM and therefore the biological oxidation occurring after 5 days in a standard $BOD_5$ measurement equates to 62.5% conversion. In the half-reaction for the reduction of oxygen to water;

$$O_2 + 4H^+ + 4e^- \rightarrow 2H_2O \qquad (6)$$

each mole of oxygen accepts four electrons (equation 6). In a standard 300 ml sample bottle the biological oxygen demand equates to 1.875 mmol of $O_2$, which is equivalent to 7.50 mFaraday of charge or 724 coulomb. Thus, in the case of a pure substrate, the BOD can be expressed as an equivalent of charge and in the method of this invention this quantity is experimentally determined from bulk electrolysis of the reduced mediator or from the potentiometric shift.

EXAMPLE 13

Effect of Alternative Microorganism *P.vulgaris* cells were cultured overnight in a trypticase soy growth broth, harvested and resuspended in a phosphate buffered saline solution (0.05M $KH_2PO_4/K_2HPO_4$ pH7 and 0.1M KCl) to an optical density ($OD_{600}$) of 5.62. The amount of charge, required for reoxidising microbially reduced mediator incubated in the presence and the absence of exogenous substrate ($BOD_5$ 9 standard) after a 60 minute incubation, was measured using the bulk electrolysis with coulometry method and are shown in Table 8.

TABLE 8

Response with *P. vulgaris*

| Run # | $OD_{600}$ | Fe(III)/$\mu$mol | $Q_{sub}$ | Time | $Q_{1\%}$/coulomb |
|---|---|---|---|---|---|
| pv08 | 5.620 | 523 | 1.683 | 60 | 1.473 |
| pv09 | 5.620 | 523 | 1.683 | 60 | 1.464 |
| pv10 | 5.620 | 523 | 1.683 | 60 | 1.548 |
| pv05 | 5.620 | 523 | 0 | 60 | 0.473 |
| pv06 | 5.620 | 523 | 0 | 60 | 0.500 |
| pv07 | 5.620 | 523 | 0 | 60 | 0.567 |

The results in Table 8 demonstrate that a more uniform conversion is obtained when *P.vulgaris* is used as the biological catalyst. However the conversion of substrate is less than that was achieved when *E.coli* was used. At 60 minutes, the conversion achieved by *P.vulgaris* is 55%.

EXAMPLE 14
Reduction of Mediator with Varying Incubation Times

Following a procedure identical to that described in Example 9, the substrate conversion by *P.vulgaris* at various incubation times was investigated. The results, using $BOD_5$ 45 standard solutions, are shown in Table 9.

TABLE 9

*P. vulgaris*; Effect of Incubation Time

| Run # | $OD_{600}$ | Fe(III)/$\mu$mol | $Q_{sub}$ | Time | $Q_{1\%}$/coulomb |
|---|---|---|---|---|---|
| 130 | 5.70 | 533 | 8.905 | 60 | 5.272 |
| 131 | 5.70 | 533 | 8.905 | 60 | 5.586 |
| 134 | 5.70 | 533 | 8.905 | 90 | 6.478 |
| 135 | 5.70 | 533 | 8.905 | 90 | 6.478 |
| 138 | 5.70 | 533 | 8.905 | 120 | 7.050 |
| 139 | 5.70 | 533 | 8.905 | 120 | 7.057 |
| 142 | 5.70 | 533 | 8.905 | 240 | 8.860 |
| 143 | 5.70 | 533 | 8.905 | 240 | 8.778 |
| 132 | 5.70 | 533 | 0 | 60 | 0.528 |
| 133 | 5.70 | 533 | 0 | 60 | 0.539 |
| 136 | 5.70 | 533 | 0 | 90 | 0.686 |
| 137 | 5.70 | 533 | 0 | 90 | 0.695 |
| 140 | 5.70 | 533 | 0 | 120 | 0.817 |
| 141 | 5.70 | 533 | 0 | 120 | 0.821 |
| 144 | 5.70 | 533 | 0 | 240 | 1.219 |
| 145 | 5.70 | 533 | 0 | 240 | 1.237 |

At incubation times of 60, 90, 120 and 240 minutes the biological oxidation conversions were 55, 65, 70 and 89%, respectively. At this cell concentration ($OD_{600}$ 5.70) an incubation time of 90 minutes is required for a conversion equivalent to the standard 5 day BOD.

EXAMPLE 15
Reduction of Mediator with Ultra-high Cell Concentration and Anaerobic Conditions The measurements described in Example 13 were repeated except that a higher cell concentration was used. *P.vulgaris* cells were grown, harvested and resuspended in saline buffer at an $OD_{600}$ 25.2. $BOD_5$ 45 mg/l standard solutions were used as substrate and the results from this trial are set out in Table 10.

TABLE 10

Ultra-high Cell Concentration and Anaerobic Conditions

| Run # | $OD_{600}$ | Fe(III)/$\mu$mol | $Q_{sub}$/coulomb | Time | $Q_{1\%}$/coulomb |
|---|---|---|---|---|---|
| 163 | 25.2 | 533 | 8.904 | 60 | 9.717 |
| 162 | 25.2 | 533 | 0.000 | 60 | 2.271 |

In comparison to the results shown in Table 9 the cell concentration in Table 10 has increased by a factor of four. The conversion achieved after 60 minutes (84%) at $OD_{600}$ 25.2 is very similar to what previously took 240 minutes at $OD_{600}$ 5.70. A linear relationship between cell density and conversion suggests that the cell concentration is the rate limiting factor in the oxidation of substrate and these results indicate the incubation time will continue to decrease as the cell concentration is increased.

REFERENCES

American Public Health Association (APHA). (1995) Standard Methods for the Examination of Water and Wastewater (19th edn.)

Baronian, K. H. R., and Pasco, N. F. (1993) Development of a Microbial Sensor for Biochemical Oxygen Demand. AEI Science Report. Contract Number AEI205. Foundation for Research, Science and Technology.

Bennetto, H. P., Stirling, J. L., Tanaka, K. and Vega, C. A. (1983) Biotechnology and Bioengineering 25, 559–568

Hach Chemical Company (1977) Manometric BOD apparatus Model 2173A

Hach Company (1990) Introduction to BOD. Technical Information Series-Booklet No. 7

Ramsey, G. And Turner A. P. F. (1988) *Analytica Chimica Acta* 215, 61–69

Thurston, C. F., Bennetto, H. P., Delaney, C. M., Mason, J. R, Roller, S. D. and Stirling, J. L. (1985) Journal of General Microbiology 131, 1393–1401

What is claimed is:

1. A method for measuring the quantity of a sample substrate consumed in a microbially catalysed biochemical reaction which comprises:
   conducting said biochemical reaction by incubating said sample substrate in an aqueous medium with an excess of a microorganism and an excess of a mediator which has the ability to reversibly react at an electrode in said biochemical reaction,
   continuing said incubation until said sample substrate is oxidised to a predetermined end point,
   measuring reduction of said mediator in said incubation, and
   correlating said reduction of said mediator to a corresponding oxidation of said sample substrate to thereby measure the quantity of sample substrate consumed in said biochemical reaction.

2. A method as claimed in claim 1 which is used to determine the biochemical oxygen demand (BOD) of said sample substrate.

3. A method as claimed in claim 1 wherein said reduction of said mediator is measured by reoxidising said mediator and measuring a charge required for doing so.

4. A method as claimed in claim 3 wherein said reoxidation of mediator and measurement of charge are carried out in a bulk electrolysis cell.

5. A method as claimed in claim 1 which is used to determine biological toxicity of said sample substrate.

6. A method as claimed in claim 1 wherein said incubation is conducted under anaerobic conditions.

7. A method as claimed in claim 6 wherein said anaerobic conditions are maintained by sparging an incubation container in which said incubation is carried out with oxygen free nitrogen.

8. A method as claimed in claim 1 wherein said predetermined end point is reached when the rate of change in reduced mediator to oxidised substrate ratio is minimal.

9. A method as claimed in claim 1 wherein said sample substrate and said mediator are separated from said microorganism before measuring the reduction of said mediator.

10. A method as claimed in claim 1 wherein said reduction of said mediator is measured by an electrochemical method.

11. A method as claimed in claim 10 wherein the measured charge is converted to a standard BOD measurement.

12. A method as claimed in claim 1 wherein said reduction of said mediator is measured by an optical method.

13. A method as claimed in claim 1 wherein said microorganism is a member of the group consisting of *Escherichia coli, Proteus vulgaris, Torulopsis candida, Bacillus subtilis, Trichosporon cutaneum* and *Saccharomyces cerevisiae*.

14. A method as claimed claim 1 wherein said mediator is a member of the group consisting of benzoquinone, dichlorophenolindophenol, methylene green, methylene blue, phenazine methosulphate, potassium hexacyanoferrate (III), resorufin, thionine, and toluidene-blue-O.

15. A method as claimed in claim 1 wherein said incubation is terminated by filtering said mediator, sample substrate and microorganism through a filter whose pore size is such that the mediator is in the filtrate and the microorganism is in the retentate.

* * * * *